United States Patent [19]

Lin et al.

[11] Patent Number: 4,552,976
[45] Date of Patent: Nov. 12, 1985

[54] PROCESS FOR OXIDATIVE DICARBONYLATION OF BUTADIENE

[75] Inventors: Jiang-Jen Lin, Round Rock; John F. Knifton, Austin, both of Tex.

[73] Assignee: Texaco Inc., White Plains, N.Y.

[21] Appl. No.: 644,470

[22] Filed: Aug. 27, 1984

[51] Int. Cl.$^4$ ............................................. C07C 67/38
[52] U.S. Cl. ................................... 560/204; 502/184; 502/185; 560/190
[58] Field of Search ............... 560/204; 502/184, 185

[56] References Cited

U.S. PATENT DOCUMENTS

| | | | |
|---|---|---|---|
| 3,393,136 | 7/1968 | Fenton et al. | 560/204 |
| 3,397,225 | 8/1968 | Fenton | 560/204 |
| 3,397,226 | 8/1968 | Fenton | 560/204 |
| 3,755,421 | 8/1973 | Fenton et al. | 560/204 |
| 4,230,881 | 10/1980 | Romano et al. | 560/193 |
| 4,269,781 | 5/1981 | Vanderspurt et al. | 260/410.9 R |
| 4,281,173 | 7/1981 | Kesling | 560/204 |
| 4,281,174 | 7/1981 | Current | 560/204 |

*Primary Examiner*—Natalie Trousof
*Assistant Examiner*—Vera C. Clarke
*Attorney, Agent, or Firm*—Jack H. Park; Kenneth R. Priem; Cynthia L. Kendrick

[57] ABSTRACT

This invention relates to the carbonylation of olefins. More particularly it involves the carbonylation of aliphatic conjugated diolefins such as 1,3-butadiene to form adipic acid precursors such as, for example, dimethyl hex-3-ene-1,6-dioate by a process comprising reacting said 1,3-butadiene with carbon monoxide and oxygen in the presence of a hetergeneous palladium catalyst, a copper-containing compound and a lithium-containing compound.

8 Claims, No Drawings

PROCESS FOR OXIDATIVE DICARBONYLATION OF BUTADIENE

FIELD OF THE INVENTION

This invention relates to the carbonylation of conjugated aliphatic diolefins. More particularly this invention relates to a novel heterogenous palladium catalyst for the carbonylation of 1,3-butadiene to hexenedioic acids and their esters, including dimethyl hex-3-ene-1,6-dioate. Adipic acid can then be produced from said hex-3-ene-1,6-dioate ester by successive reduction/hydrolysis steps.

BACKGROUND OF THE INVENTION

The addition of carbon monoxide to olefins (carbonylation) has long been considered in the art to be a highly attractive route to a number of commercially valuable chemical products. It is known in the art to prepare unsaturated aliphatic carboxylic acids and their esters by the catalytic oxidative carbonylation of a diolefin. More particularly, it is known to synthesize aliphatic carboxylic acids and their esters by reacting carbon monoxide, oxygen and a conjugated aliphatic diolefin such as 1,3-butadiene, isoprene, 2,3-dimethylbutadiene, 1,3-pentadiene and the like under elevated temperature and pressure conditions in the presence of various catalysts, often in the presence of dehydrating agents. One useful diester is dimethyl hex-3-ene-1,6-dioate which is a precursor for adipic acid. Adipic acid is a large volume chemical used, for example, in making nylon-66 polymer for fibers and plastics, as well as in polyurethane foams.

Some of the early patents in the field, such as U.S. Pat. Nos. 3,397,226, 3,397,225, 3,481,845 and 3,755,421, demonstrate the use of catalysts comprising a platinum group metal salt or chelate and a multivalent heavy metal salt which functions as a redox agent for the oxidative carbonylation of hydrocarbon olefins to produce esters of unsaturated carboxylic acids, esters of dicarboxylic acids and esters of beta-alkoxy-substituted carboxylic acids.

In U.S. Pat. No. 4,281,173 there is disclosed a process for the preparation of unsaturated diesters in the presence of a catalytic amount of a platinum group metal compound, a copper or iron oxidant salt compound, a soluble vanadium salt or a stoichiometric amount of a dehydrating agent. An anhydrous halogen-containing acid may optionally be included. Butadiene is the starting substrate in this patent, but the examples disclose only the use of a homogeneous palladium catalyst system, the effect of supported palladium systems remains unknown.

The invention of international publication PCT WO80/00250 comprises the carbonylation of conjugated diolefins, such as 1,3-butadiene, by the addition of carbon monoxide and alcohol of the formula ROH in the presence of a palladium(II) salt, a copper(II) salt and a base. This synthesis requires the use of stoichiometric quantities of copper(II) salt component, but does not require an oxygen component.

In another process which is disclosed in *J. Org. Chem.* 1979, 44(20), 3474–82, methoxycarbonylation of a variety of olefins with methanol and carbon monoxide takes place in the presence of palladium, using stoichiometric amounts of copper(II) chloride as a reoxidant, and sodium butyrate as a buffer. Different aliphatic carboxylic acid diesters were formed in varying yields depending on the choice of diolefin and the carbon monoxide pressure. The reaction usually resulted in the addition of two carbomethoxy functions to the double bond.

In Japanese Pat. No. 8248,942 to Ube Industries, Ltd. diesters were prepared by the addition of carbon monoxide, oxygen and alcohols to conjugated dienes in the presence of, again, PdCl$_2$ and CuCl$_2$ along with BuNH$_2$ in dioxane.

In *J. Am. Chem. Soc.* 98, 1810 (1976), James and Stille provide much data on the yields of various esters using different cyclic and acyclic olefin reactants. They also discuss the effects of some of the cocatalysts, etc. used in many of these reactions and yields of products. Again palladium(II) chloride is employed as catalyst, and stoichiometric amounts of copper(II) chloride is used as reoxidant. The effect of added base is also discussed.

A study reported in *J. Org. Chem.* 37 2034 (1972) discussed experiments which demonstrate that in a palladium redox system, optimum results are achieved by restricting both amounts of excess hydrogen ion and chloride ion.

U.S. Pat. No. 4,230,881 discloses a binary system for preparation of organic esters such as dimethyl oxalate in which the principal member is a palladium complex and the cocatalyst is preferably an organic compound having an acidic nature, no matter how weak. With this system esters are prepared without employing any oxygen and without formation of water.

In U.S. Pat. No. 4,269,781 there is disclosed a process for producing and recovering alkyl nonadienoate which comprises the steps of reacting 1,3-butadiene with carbon monoxide and an alkanol containing between about 0.5–10 weight percent of water, in the presence of a catalyst complex of palladium and tertiary phosphine ligand, to yield a liquid phase product mixture containing alkyl nonadienoate; contacting the product mixture with a hydrocarbon solvent to form two liquid phases and separating the two liquid phases and recovering alkyl nonadienoate from the hydrocarbon solvent phase.

U.S. Pat. No. 4,281,174 discloses a catalyst system for preparing dialkyl oxalates by the oxidative carbonylation of alcohols which comprises reacting CO and air with an alcohol in the presence of a catalyst comprising palladium in complex combination with a ligand, a small amount of quinone, and a redox agent. This patent teaches that the quinone component helps improve yields.

In *J. Mol. Cat.* 18 (1983) 109-112 there is a report by Kiji, et al. on improvement in the activity of palladium catalysts for the dimerization-monocarbonylation of butadiene comprising reportedly improving the catalytic activity of the Pd(OAC)$_2$/R$_3$P system by adding maleic anhydride. Although not fully understood, it was reasoned that the maleic anhydride appears to stabilize the Pd(O) species through coordination after the catalytic cycle is completed.

In many processes known in the art separation of the high boiling aliphatic carboxylic acid or ester product from the catalyst system can be difficult. It would be advantageous to devise a catalyst system which is heterogenous, which improves the product distribution to desired carboxylic acid and which improves ease of product/catalyst separation. A supported (palladium-containing) catalyst system which allowed for easier separation of product from catalyst by filtration would be more efficient and far more attractive commercially.

Furthermore, the selection of a suitable support for such a palladium catalyst system may be made so as to improve both the productivity to desired carboxylic acid/ester derivative and the selectivity to said desired product or products.

It would be extremely advantageous if such a system produced a higher yield of linear aliphatic carboxylic acid ester precursors of adipic acid.

SUMMARY OF THE INVENTION

The present invention provides a process for the improved production of linear hexenedioic acid esters by the oxidative carbonylation of butadiene with carbon monoxide and an alkanol to form adipic acid precursors, including dialkyl hexenedioates, and by-products, including alkyl 5-methoxy-3-pentenoate, dialkyl carbonate, dialkyl oxalate and 4-vinyl- cyclohexene in the presence of a catalyst comprising palladium on a suitable support in the presence of a copper-containing compound and a lithium-containing compound.

This invention demonstrates improved linearity of product, improved ratio of desired to undesired products, and improvement in ease, efficiency and commercial attractiveness of means of separation of product.

DESCRIPTION OF THE INVENTION

One or more objects of the present invention are accomplished by the process of the instant invention comprising reacting a conjugated aliphatic diolefin with carbon monoxide, oxygen and an alkanol over a heterogenous, supported, palladium catalyst in the presence of a copper-containing compound and a lithium-containing compound in a reaction vessel and subjecting the contents of the charged vessel to a carbon monoxide pressure and a temperature sufficient to effect the carbonylation reaction.

In accordance with the invention aliphatic diolefins having conjugated double bonds of the formula:

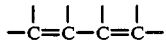

wherein each carbon is bonded to hydrogen or a hydrocarbyl group, is converted by the palladium-catalyzed addition to said double bond of carbon monoxide, oxygen and an alkanol, to produce aliphatic, unsaturated dicarboxylic esters in which the conjugated double bonds have been transformed into a moiety having the formula:

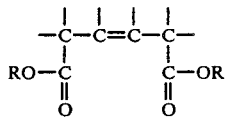

wherein R is an alkyl group. The process comprises passing the aliphatic conjugated diolefin, carbon monoxide and oxygen together with alkanol over a heterogenous supported palladium catalyst in the presence of cocatalysts which preferably contain a copper compound and lithium compound. The reactants and catalyst components are charged to a reaction vessel and, in the absence of water, subjected to a carbon monoxide pressure and temperature for a sufficient period of time to effect the desired carbonylation reaction. In the specific use of the diolefin 1,3-butadiene, the carbonylation reaction can be represented by the following equation:

$$CH_2=CHCH=CH_2 + CO + O_2 + CH_3OH \xrightarrow[\text{Cu Compound}]{\text{Supported Pd}}$$

$CH_3OOCCH_2CH=CHCH_2COOCH_3 +$ $CH_3OCH_2CH=CHCH_2COOCH_3$ and

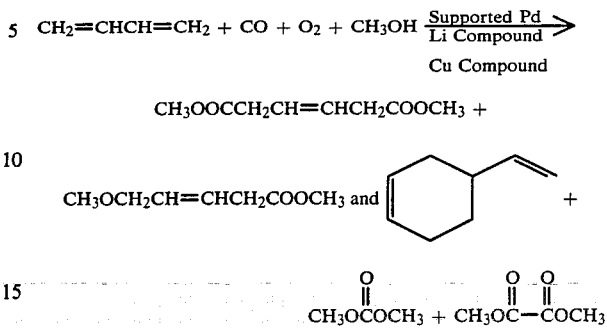

Generally the reaction between the aliphatic conjugated diolefin, carbon monoxide, oxygen and alkanol may be carried out in an autoclave or other appropriate reactor. Although the order of addition of reactants and catalyst components may vary, a general procedure is to charge the supported palladium catalyst, copper-containing cocatalyst, lithium-containing cocatalyst, aliphatic conjugated diolefin, alkanol and optional dehydrating agent to an appropriate reactor, such as a stainless-steel, magnedrive reactor, then introduce the proper amount of carbon monoxide and oxygen and increase the pressure and temperature to a desired level for an appropriate period to produce the desired aliphatic carboxylic acid derivative.

Diolefins suitable for use in the present invention are aliphatic conjugated diolefins containing four to twelve atoms per molecule and having the general formula:

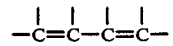

wherein each carbon is bonded to hydrogen or a hydrocarbyl group.

Suitable aliphatic conjugated diolefins include 1,3-butadiene, piperylene, 1,3-hexadiene, isoprene, 2,4-hexadiene, 2-methyl-1,3-pentadiene, 3-methyl-1,3-pentadiene, 1,3-cyclohexadiene, 2,4-dimethyl-1,3-pentadiene, 1,3-cyclooctadiene, 2,5-dimethyl-2,4-hexadiene, 2,3-dimethyl-2,4-hexadiene and the like. The preferred aliphatic conjugated diolefin for the practice of this invention is 1,3-butadiene.

The alcohol coreactants used in these syntheses are aliphatic monohydric alkanols each containing one to twenty carbon atoms per molecule. Suitable aliphatic monohydric alkanols include methanol, ethanol, n-propanol, iso-propanol, tert-butanol, n-butanol, n-hexanol, n-decanol, n-dodecanol and the like. The preferred aliphatic monohydric alkanol coreactant is methanol.

As mentioned hereinabove a palladium-containing catalyst compound is employed in the process of the invention which together with the particular cocatalysts provides a catalyst system which demonstrates an increase in selectivity for linear carboxylic acid ester products and which allows for ease of separation, a feature which is commercially attractive and desired in the art. Thus, the palladium-compound is preferentially present wherein the palladium is bonded to an inert support material such as alumina, silica-alumina, silica gel, kaoline, keiselguhr, zirconium oxide, titania, barium carbonate, silicalite, as well as certain zeolitic silica-aluminas such as a 4A-molecular sieve, and certain activated carbons. The preferred palladium-containing catalyst compound is palladium-on-activated carbon. In this case, the palladium concentration on the activated carbon support may vary from 0.1 wt % to at least 20 wt %. This is the range normally employed, with the preferred range being 0.5 wt % to 5.0 wt %.

The support may be in the form of powders, pellets, spheres, shapes and extrudates. They should also be of suitable porosity such that they may be employed in fixed or fluidized bed ratios. In the process of this invention palladium on graphite (1%) was found to be the preferred form of the catalyst. Based on converted butadiene, the adipic acid precursor hex-3-ene-1, 6 dioate was produced at 85% selectivity.

The palladium-containing precursor compound to be dispersed upon the solid support may be impregnated on said supports in the form of a bivalent palladium-containing salt, possibly as the salt of a carboxylic acid such as palladium acetate, palladium propionate, or as palladium acetylacetonate, palladium nitrate and the like. Alternately it can be added in the form of a palladium halide, such as palladium(II) chloride.

Generally, said palladium-containing catalyst system is prepared by first dissolving or slurrying the selected palladium salt, halide, etc., e.g. palladium(II) chloride, with a suitable solvent system and subsequently impregnating the selected inert support or carrier with the palladium-containing mixture. These solutions or slurries may be poured onto the carrier, or the solid carrier may be immersed in an excess of the liquid solution or slurries, with the excess being subsequently removed.

The impregnated support is then maintained at a temperature sufficient to volatize the solvent component, e.g. at a temperature between 100° C. and 500° C., to permit drying of the composite solid catalyst. A vacuum may also be applied to the catalyst in order to volatize the solvent, although use of vacuum is not essential. During this stage of the process the volatile solvent evaporates from the solid catalytic products, and the palladium component remains on the support.

The solvent which may be used to dissolve the palladium-containing compound prior to impregnation onto the support should be a liquid of relatively low boiling point such as, for example, about 150° C. or less. A preferable group of solvents include mineral acid solutions such as hydrochloric acid and nitric acid, carboxylic acids such as acetic acid and propionic acid, halogenated solvents like chloroform and carbon tetrachloride, ketones such as acetone and methyl isobutyl ketone, alcohols such as methanol, iso-propanol and tert-butanol, aromatics such as benzene, toluene and xylene, as well as certain heterocyclic solvents like pyridine and N-methylpyrrolidone. The choice of solvent is dependent upon the nature of the palladium-containing compound to be used for impregnation.

In accordance with this invention a copper-containing compound is used as a cocatalyst. The copper-containing cocatalyst can be added to the reactor in the form of a salt of copper such as a halide, sulfate, trifluoroacetate, nitrate, naphthalenate, hex-3-endioates or acetate. Copper salts which work include, but are not limited to copper(II) chloride, copper(II) bromide, copper(II) sulfate, cuprous chloride hydrate, copper(II) trifluoroacetate, copper(II) acetate, copper(II) triflate, copper(II) fluorosulfonate, copper(I) chloride and copper(I) sulfate.

The preferred compound is copper(II) chloride.

In the process of this invention a lithium-containing cocatalyst is used in addition to the copper-containing cocatalyst. The lithium-containing compound is selected from the group consisting of salts of lithium from the group including lithium halides, sulfates, nitrates and acetates. Examples include lithium chloride, lithium bromide, lithium iodide and lithium acetate. The preferred lithium-containing compound is lithium chloride.

Optionally a dehydrating agent may also be added to the reaction mixture in the practice of this invention. Suitable dehyrating agents that may be used during the preparation of said aliphatic carboxylic acid esters include certain acetals and ketals. These may include acetaldehyde dimethyl acetal, benzaldehyde dimethyl acetal and formaldehyde dimethyl acetal. Suitable ketals can be 2,2-dimethoxypropane, dimethoxymethane and the like. Said dehydrating agent may be used in a wide range of ratios compared with the quantity of aliphatic conjugated diene charge, but in the case of 1,3-butadiene carbonylation, preferably 1-2 moles, or more, of dehydrating agent, such as 2,2-dimethoxypropane, are employed per mole of 1,3-butadiene charged.

The process of the present invention can be suitably performed by introducing the oxygen, carbon monoxide and alcohol at a desired pressure into contact with the diolefin, preferably butadiene, optional dehydrating agent, the supported palladium catalyst, copper-containing cocatalyst and lithium-containing cocatalyst and heating to the desired temperature.

In general a carbon monoxide pressure of about 50 psig to about 5000 psig partial pressure and preferably about 500 psig to about 1800 psig is employed. At least stoichiometric quantities of carbon monoxide are generally employed. However, an excess of carbon monoxide may be employed, for example, particularly in continuous processes. Where a large excess of or high carbon monoxide requirements are generally utilized, a suitable recycle of the unreacted carbon monoxide may be employed.

The partial pressure of oxygen is generally selected so that the molar ratio of carbon monoxide to oxygen is in the range 1:1 to 100:1. A carbon monoxide to oxygen ratio in the range of 5:1 to 20:1 has been employed in this work for the synthesis of hexenedioic acid esters from 1,3-butadiene, and is considered to be the preferred range.

The reaction will proceed at temperatures above 25° C. It is generally preferred to operate the process at temperatures in the range of 80° C. to 150° C. to obtain a convenient rate of reaction with the particular diolefin.

The reaction time is generally dependent upon the diolefin being reacted, temperature, pressure and on the amount and type of catalyst, cocatalyst and dehydrating agent being employed. Reaction time will vary dependent on whether the process is continuous or batch and may vary from one to 15 hours. Reaction time for butadiene is generally about two hours.

The quantity of palladium catalyst employed in the instant invention is not critical and may vary over a wide range. In general, the carbonylation process is desirably conducted in the presence of a catalytically effective quantity of the active palladium species which gives the desired ester products in reasonable yields.

The quantity of copper-containing catalyst employed in the instant invention is not critical and may vary over a wide range. In general, the carbonylation process is desirably conducted in the presence of a catalytically effective quantity of the active copper species which along with palladium and lithium gives the desired ester products in reasonable yields. The reaction proceeds when employing concentrations of copper-containing compound of between 0.1 wt % and 50 wt %, with the preferred range being 0.1 wt % to 1 wt % and optimally about 0.5 wt %. Higher concentrations of copper-containing compound may be used to the extent of 50 wt %.

The quantity of lithium-containing catalyst employed in the instant invention is not critical and may vary over a wide range. In general, the carbonylation process is desirably conducted in the presence of a catalytically effective quantity of the active lithium species which along with palladium and lithium gives the desired ester products in reasonable yields. The reaction proceeds when employing concentrations of lithium-containing compound of between 0.0001 wt % and 1.0 wt %, with the preferred range being 0.001 wt % to 0.1 wt % and optimally about 0.005 wt %. Higher concentrations of lithium-containing compound may be used to the extent of 1.0 wt %.

The ratio of supported palladium-containing compound to copper-containing cocatalyst to lithium-containing cocatalyst is not critical. Good results are obtained using a weight ratio of Pd:Cu:Li of about 0.01:1.0:0.005.

In reacting 1,3-butadiene, carbon monoxide, oxygen and an alcohol in the presence of the catalyst to form a hexenedioic acid diester, whether accomplished in continuous operations or batch experiments, the carbon monoxide may also be used in conjunction with up to 50% by volume of one or more other gases. These other gases may include one or more inert gases such as nitrogen, argon, neon and the like, or they may include gases that may, or may not, undergo reaction under CO carbonylation conditions such as carbon dioxide, hydrogen, hydrocarbons such as methane, ethane, propane and the like, ethers such as dimethyl ether, methylethyl ether and diethyl ether, and acid esters such as methyl acetate.

The 1,3-butadiene carbonylation process disclosed herein leads to the formation of two classes of products. The primary product is the hexenedioic acid diester, dimethyl hex-3-ene-1,6-dioate, which can be reduced and hydrolyzed to adipic acid. By-products include 5-methoxy-3-pentenoate, dimethyl carbonate and dimethyl oxalate.

The benefits of the improved 1,3-butadiene carbonylation process using the supported palladium catalyst, copper-containing cocatalyst, lithium-containing cocatalyst and optional dehydrating agent are:

(a) increased productivity of hexenedioic acid ester product (b) ease of separation of said hexenedioic acid ester from the palladium catalyst component.

The process of this invention can be conducted in a batch, semi-continuous or continuous fashion. The solid catalyst may be employed as a fixed bed. The reactor may consist of a series of catalyst beds or the catalyst may be placed in tubes with a heat exchange medium around the tubes. So as to provide certain operating advantages, the metal content of the catalyst may be varied through the reactor bed, and the reactants may be passed up-flow or down-flow through the reactor.

To ensure maximum yields of desirable products, contact between the liquid reaction mix and any iron-rich metal surfaces should be limited wherever possible during the carbonylation step. One means by which this contact can be minimized is by carrying out the olefin carbonylation reaction in a glass-lined reactor. A second, alternative method is to have the carbonylation reactor lined with some other inert materials, such as by using a silver-lined reactor, prior to effecting the diene carbonylation. Further alternatives include the use of titanium-lined pressure reactors, tantalum-lined reactors, and reactors having Hastelloy alloy or copper-nickel alloy surfaces.

Generally, operating conditions can be adjusted to optimize the formation of any desired linear aliphatic carboxylic diester product, and said materials may be recovered by methods well known in the art, such as filtration, distillation, fractionation, extraction and the like.

The products of this improved catalyst system have been identified by one or more of the following analytical procedures, viz, gas-liquid phase chromatography (glc), infrared (ir) mass spectrometry, nuclear magnetic resonance (nmr) and elemental analysis, or a combination of these techniques. All temperatures are in degrees centigrade and all pressures in pounds per square inch gauge (psi). Having described the inventive process, the following examples are submitted to supply specific and illustrative embodiments.

It is to be understood these examples are illustrative and the invention is not to be limited thereby:

The following equation describes the basic reaction described in Examples A–J. The various products are labeled with Roman numerals for reference.

$$CH_2=CHCH=CH_2 + CO + O_2 + CH_3OH \xrightarrow{catalyst}$$

$$CH_3OOCCH_2CH=CHCH_2COOCH_3 +$$
(I)

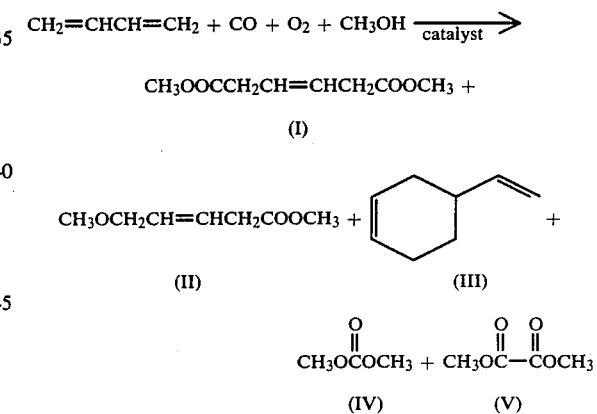

(II)    (III)    (IV)    (V)

EXAMPLE A

To a 300 ml stainless-steel, magnedrive reactor was charged palladium (1.0 wt %) on graphite (1.0 g), copper(II) chloride, hydrate (1.2 g) lithium chloride (0.084 g), methanol (0.96 g) and 2,2-dimethoxypropane (20 g). The autoclave was sealed and then 20.0 g of 1,3-butadiene was charged and followed by pressuring CO (500 psi) and $O_2$ (100 psi). The system was heated to 100° C. and pressure was raised to 1500 psi with CO. These conditions were held for 2 hours. During the reaction process, the pressure dropped to 1250 psi. The reactor was cooled to room temperature and an off-gas sample was taken. The excess gas was vented and a brown liquid product with solid catalysts at the bottom was recovered (33.3 g).

The glc analysis of liquid products and off-gas samples indicated the following product selectivities:

| | |
|---|---|
| dimethyl hex-3-ene-1,6-dioate (I) | 28% |
| methyl 5-methoxy-3-pentenoate (II) | 5% |
| 4-vinyl-1-cyclohexene (III) | 22% |
| dimethyl carbonate (IV) | 31% |
| dimethyl oxalate (V) | 13% |

Estimated selectivity to dimethyl hex-3-ene-1,6-dioate (basis butadiene carbonylated) is 85%.
The off-gas analysis showed:

| | |
|---|---|
| carbon monoxide | 92.6% |
| carbon dioxide | 1.1% |
| total heavies material | 5.2% |

Examples B–J were carried out using the same procedure as described in Example A. Results are shown in Table I. The copper-containing and lithium-containing cocatalysts were the same throughout as that used in Example A, except for Example E where no lithium cocatalyst was employed. Examples B, C and D use supports other than graphite for the palladium.

TABLE I
SYNTHESIS OF DIMETHYL HEX-3-ENE-1,6-DIOATE FROM BUTADIENE, CARBON MONOXIDE AND METHANOL

| Example | Pd-Catalyst | Copper Cocatalyst | LiCl Co-catalyst | MeOH | 2,2-di-methoxy-propane | Reaction conditions | Temp. Time | Wt. gain | Product Selectivities | | | | |
|---|---|---|---|---|---|---|---|---|---|---|---|---|---|
| | | | | | | | | | I | II | III | IV | V |
| B | 0.5% Pd on Kaolin (2.0 g) | CuCl$_2$.2H$_2$O 1.20 g | 0.084 g | 0.96 g | 20 g$^a$ | 1500 psi; CO/O$_2$ = 7 | 100° C. 2 hr. | — | 3 | 1 | 14 | 72 | 7 |
| C | 0.5% Pd on Kaolin (2.0 g) | CuCl$_2$.2H$_2$O 1.20 g | " | " | 20 g$^a$ | 1500 psi; CO/O$_2$ = 7 | 100° C. 2 hr. | 0 | — | — | 13 | 84 | — |
| D | 0.5% Pd on Al (2.0 g) | CuCl$_2$.2H$_2$O 1.20 g | " | " | 20 g$^a$ | 1500 psi; CO/O$_2$ = 15 | 100° C. 5 hr. | 3.6 g | — | — | — | 81 | — |
| E | 1% Pd on graphite (1.0 g) | CuCl$_2$.2H$_2$O 1.20 g | 0 | " | 20 g$^a$ | 1500 psi; CO/O$_2$ = 15 | 100° C. 2 hr. | 4.1 g | 15 | 5 | 16 | 76 | 3 |
| F | 1% Pd on graphite (1.0 g) | CuCl$_2$.2H$_2$O 1.20 g | 0.084 g | 10 g | 0$^a$ | 1500 psi; CO/O$_2$ = 15 | 100° C. 2 hr. | 3.0 g | 26 | 19 | 33 | 8 | 1 |
| G | 1% Pd on graphite (1.0 g) | CuCl$_2$.2H$_2$O 1.20 g | " | 0.96 g | 20 g$^a$ | 2000 psi; CO/O$_2$ = 20 | 100° C. 2 hr. | 2.6 g | 21 | 3 | 15 | 42 | 10 |
| H | 1% Pd on graphite (1.0 g) | CuCl$_2$.2H$_2$O 1.20 g | " | " | 20 g$^b$ | 875 psi; CO/O$_2$ = 8 | 100° C. 2 hr. | 5.8 g | 8 | ~0 | 30 | 61 | ~0 |
| I | 1% Pd on graphite (1.0 g) | CuCl$_2$.2H$_2$O 1.20 g | " | " | 20 g$^b$ | 825 psi; CO/O$_2$ = 8 | 80° C. 2 hr. | 2.2 g | 9 | 2 | 15 | 75 | 0 |
| J | 1% Pd on graphite (1.0 g) | CuCl$_2$.2H$_2$O 1.20 g | " | " | 20 g$^b$ | 2000 psi; CO/O$_2$ = 20 | 80° C. 2 hr. | 0.5 g | 2 | 0 | 14 | 75 | 1 |

(a) Butadiene used (20 g), except (b) 40 g

It may be noted from a consideration of the data in Table I that:

(1) In Examples A–D, showing the use of various palladium catalyst components on different supports, the palladium-on-graphite catalyst gave a significant improvement in selectivity to desired product, dimethyl hex-3-ene-1,6-dioate(I)-Example A.

(2) Production of desired dimethyl hex-3-ene-1,6-dioate(I) is lower, and selectivity to less desirable dimethyl carbonate is higher, when no lithium cocatalyst is used (see Example E).

(3) The ratio of desirable dimethyl hex-3-ene-1,6-dioate(I) to less desirable methyl 5-methoxy-3-pentenoate(II) is lower in the absence of the dehydrating agent, 2,2-dimethoxypropane (see Example F).

(4) Productivity to desired adipic acid precursor-I-is lower when less oxygen is used (see Example G).

(5) Productivity to desired hexenedioic acid ester-I-is lower when less carbon monoxide is used, and the weight ratio of I/IV+V is also lower (see Example H).

(6) Lower operating temperatures (Examples I and J) lead to lower weight gains of liquid products.

What is claimed is:
1. A process for oxidative carbonylation of aliphatic conjugated diolefins containing 4 to 12 carbon atoms per molecule of the formula:

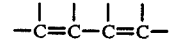

wherein each carbon is bonded either to hydrogen or a hydrocarbyl group, by reaction with carbon monoxide and oxygen in the presence of an alkanol coreactant containing 1 to 20 carbon atoms per molecule, to form an aliphatic dicarboxylic acid ester having the formula:

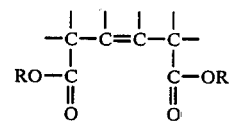

wherein R is a saturated alkyl group, said process being conducted in the presence of a heterogeneous supported palladium catalyst, a copper-containing cocatalyst and a lithium-containing cocatalyst, at a temperature of 80° C. to 150° C. and a pressure of from 500 psi to 1800 psi to effect the desired carbonylation reaction, wherein the carbon monoxide to oxygen ratio is from 5:1 to 20:1, the palladium catalyst is deposited on said support in a concentration range of 0.1 to 20 wt %, the concentration of copper-containing cocatalyst is between 0.1 wt % and 50 wt % and the concentration of lithium-containing cocatalyst is between 0.0001 wt % and 1.0 wt %.

2. A process according to claim 1 wherein the conjugated diolefin is 1,3-butadiene, the alkanol coreactant is methanol coreactant, the supported palladium catalyst comprises 1% palladium on graphite; the copper-containing cocatalyst comprise a copper salt from the group consisting of cupric chloride, cuprous bromide and cuprous chloride hydrate; the lithium-containing cocatalyst comprises a lithium salt from the group consisting of lithium iodide, lithium bromide and lithium chloride; the temperature is at least 25° C.; the carbon monoxide pressure is least 50 psi and the carbon monoxide to oxygen ratio is initially between 1:1 and 100:1 and the primary aliphatic dicarboxylic acid ester is hex-3-ene-1,6-dioate.

3. A process according to claim 2 further comprising producing adipic acid by subjecting the dimethyl hex-3-ene-1,6-dioate product obtained to reduction followed by hydrolysis.

4. A process according to claim 1 wherein the copper-containing cocatalyst comprises a copper salt from the group consisting of cupric chloride, cupric bromide, cupric iodide and cuprous chloride hydrate.

5. A process according to claim 1 wherein the lithium-containing cocatalyst comprises a lithium salt which is lithium chloride.

6. A process according to claim 1 wherein the support for the palladium catalyst is graphite.

7. A process according to claim 2 wherein said dimethyl hexe-3-ene-1,6-dioate product is separated from said palladium catalyst system by filtration.

8. A process for oxidative carbonylation of 1,3-butadiene, which comprises reacting 1,3-butadiene with carbon monoxide and oxygen in the presence of methanol over a heterogeneous supported palladium catalyst comprising 1% palladium graphite, in the presence of a copper-containing cocatalyst comprising a copper salt from the group consisting of cupric chloride, cuprous bromide and cuprous chloride hydrate and a lithium-containing cocatalyst from the group consisting of lithium iodide, lithium bromide and lithium chloride wherein the ratio of palladium catalyst-to copper-to lithium-containing cocatalyst is about 0.01:1.0:0.005, at a temperature of 80° C. to 150° C. and a pressure of 500 psi to 1800 psi to form dimethyl hex-3-ene-1, 6-dioate, and thereafter separating said dimethyl-hex-3-ene-1, 6-dioate from said supported catalyst by filtration, wherein the carbon monoxide to oxygen ratio is from 5:1 to 20:1.

* * * * *

UNITED STATES PATENT AND TRADEMARK OFFICE
CERTIFICATE OF CORRECTION

PATENT NO. : 4,552,976
DATED : November 12, 1985
INVENTOR(S) : Jiang-Jen Lin and John Frederick Knifton It is certified that error appears in the above-identified patent and that said Letters Patent is hereby corrected as shown below:

Column 10, Claim 2, line 60, delete "coreactant".

Signed and Sealed this

Eleventh Day of February 1986

[SEAL]

Attest:

DONALD J. QUIGG

Attesting Officer

Commissioner of Patents and Trademarks